United States Patent
Johnson et al.

(10) Patent No.: US 6,844,020 B2
(45) Date of Patent: Jan. 18, 2005

(54) SOLUTIONS OF CAROTENOIDS FOR USE IN FOODS AND PERSONAL CARE PRODUCTS

(75) Inventors: Holly Johnson, West Des Moines, IA (US); Amanda Ueltschy, Des Moines, IA (US); Jerry Newman, West Des Moines, IA (US); Anthony Newman, Fort Worth, TX (US); Jennifer Barker, Ames, IA (US); Zoraida DeFreitas, Polk City, IA (US); Rod Ausich, Des Moines, IA (US)

(73) Assignee: Kemin Foods, L.C., Des Moines, IA (US)

( * ) Notice: Subject to any disclaimer, the term of this patent is extended or adjusted under 35 U.S.C. 154(b) by 0 days.

(21) Appl. No.: 10/206,633

(22) Filed: Jul. 26, 2002

(65) Prior Publication Data

US 2004/0018279 A1 Jan. 29, 2004

(51) Int. Cl.$^7$ .............................................. A23L 1/275
(52) U.S. Cl. ..................... 426/540; 426/590; 426/599; 426/250; 424/451
(58) Field of Search ............................... 426/540, 590, 426/599, 250; 424/451

(56) References Cited

U.S. PATENT DOCUMENTS

| | | | | |
|---|---|---|---|---|
| 4,572,915 A | * | 2/1986 | Crooks | 514/458 |
| 4,693,892 A | * | 9/1987 | Hegasy et al. | 424/456 |
| 5,034,228 A | | 7/1991 | Meybeck et al. | |
| 5,084,292 A | | 1/1992 | Van Dort et al. | |
| 5,230,836 A | * | 7/1993 | Todd, Jr. | 252/407 |
| 5,437,880 A | * | 8/1995 | Takaichi et al. | 426/73 |
| 5,863,953 A | | 1/1999 | Luddecke et al. | |
| 5,972,993 A | | 10/1999 | Ptchelintsev | |
| 6,056,971 A | | 5/2000 | Goldman | |
| 6,075,058 A | | 6/2000 | Handelman | |
| 6,110,478 A | | 8/2000 | Harang | |
| 6,132,790 A | * | 10/2000 | Schlipalius | 426/540 |
| 6,287,615 B1 | * | 9/2001 | Runge et al. | 426/268 |

FOREIGN PATENT DOCUMENTS

| | | | |
|---|---|---|---|
| JP | 05247364 | * | 9/1993 |
| WO | WO 94/06310 | * | 3/1994 |

OTHER PUBLICATIONS

"Gistbrocades and SKW Trostberg from joint venture to market carotene," Performance Chemicals Aug. 1995, p. 7, vol. 10.
Wilson, Fred, "Beta Carotene Fails to Prevent Skin Cancers," Dermatolgy Times. 4/20000. Pp. 1, vol. 21.
Wilson, Fred, "Carotenoids Protect Against UV–induced Erythema," Dermatology Times. May 2000, pp 31, vol. 21.
Bluhm, Renata, Robert Branch, Philip Johnston, Richard Stein. "Aplastic Anemia Associated with Canthaxanthin Ingested for 'Tanning' Purposes," JAMA, Sep. 1990, pp 1141–1142, vol. 264, No. 9.
Lamb, Carol, "Treatment Cosmetics: Beauty with Benefits," Chemical Specialties, Mar. 1996, pp. 36–42.
"Malignant Melanoma Female/Male Death Ratios." The Lancet. Jun. 1981, pp 1419–1420.
"Lightening skin and lessening cellulite," Cosmetics & Toiletries. Apr. 1996. pp 38–41.
"Henkel launches natural carotene." Raw Materials.
Lobacheva, I. and Letchamo, W. Toxic Metals in Different Varieties of Seabuckthorn (*Hippophae rhamnoides*) Biotek Inc., Altai, Russia. Flora Labs. Inc., & Trout Lake Farm, WA. 98650.
"L'Oreal HydraSoft Deeply Softening SPF 12 Lipcolour," NERAC, No. 14, V. 29. Jul. 1999.

\* cited by examiner

*Primary Examiner*—N. Bhat
(74) *Attorney, Agent, or Firm*—Kent A. Herink; Daniel A. Rosenberg; Emily E. Harris

(57) ABSTRACT

Concentrated solutions of carotenoids in essential oils and cosmetic oils for use in foods, beverages, and personal care products. The concentrated solutions comprise between about 0.8 weight % and about 8 weight % carotenoid in the oil, or between about 15 times and about 100 times the maximum concentration reported in the prior art. The concentrated solutions are particularly suited for adding carotenoids to foods, beverages, and personal care products. An antioxidant may be added to help in preventing oxidation of the carotenoid.

4 Claims, No Drawings

SOLUTIONS OF CAROTENOIDS FOR USE IN FOODS AND PERSONAL CARE PRODUCTS

BACKGROUND OF THE INVENTION

1. Field of the Invention

The invention relates generally to food, beverage, and personal care product additives and, more specifically, to solutions of carotenoids for use in supplementing foods, beverages, and personal care products with carotenoids and for use in coloring foods and beverages.

2. Background of the Prior Art

Carotenoids are naturally-occurring yellow to red pigments of the terpenoid group that can be found in plants, algae, and bacteria. Carotenoids include hydrocarbons (carotenes) and their oxygenated, alcoholic derivatives (xanthophylls). They include actinioerythrol, astaxanthin, bixin, canthaxanthin, capsanthin, capsorubin, β-8'-apo-carotenal (apo-carotenal), β-12'-apo-carotenal, α-carotene, β-carotene, "carotene" (a mixture of α- and β-carotenes), γ-carotene, α-cryptoxanthin, β-cryptoxanthin, lutein, lycopene, violerythrin, zeaxanthin, and esters of hydroxyl- or carboxyl-containing members thereof. Many of the carotenoids occur in nature as cis- and trans-isomeric forms, while synthetic compounds are frequently racemic mixtures. The carotenes are commonly extracted from plant materials. For example, lutein extracted from marigold petals is widely used as an ingredient in poultry feed where it adds color to the skin and fat of the poultry and to the eggs produced by the poultry. Many of the carotenes are also made synthetically; much of the commercially available β-carotene has been made through synthesis.

Carotenoids are used in the pharmaceutical industry and as ingredients in nutritional supplements, most commonly to date because of their pro-vitamin A activity. They have been extensively studied as antioxidants for protection against cancer and other human and animal diseases. Among the dietary carotenoids, the focus has been on β-carotene. More recently, research has begun to elicit the broad role that other carotenoids play in human and animal health. The xanthophylls in particular have been shown to possess strong antioxidant capabilities and may be useful in reducing the risk of disease. For example, the consumption of lutein and zeaxanthin has been identified as leading to a 57 percent reduction in age-related macular degeneration (Seddon et al., 1994. *J. Amer. Med. Assoc.* 272(18): 1413–1420). Lycopene has been identified as a nutrient that is active in reducing the risk of prostate cancer.

Carotenoids have also been of wide interest as a source of added color for food and drink products and many efforts have been made to attempt to use them as "natural" colorants for foods and beverages. However, their insolubility in water, their low solubility in fats and oils, high melting points, and their sensitivity to oxidation has limited their use. Until now, it was believed that the solubility of carotenoids in oils was limited to a maximum of about 0.08%. For specific carotenoids, the reported solubility reported is 0.029% for lutein in canola oil; 0.032% for lutein in soybean oil; 0.033% for lutein in safflower oil; 0.042% for lutein in corn oil; 0.004% for zeaxanthin in corn oil; 0.05–0.08% for β-carotene in "fats and oils" (www.agsci.ubc.ca/courses/fnh/410.colour/330.htm); and 0.005% for canthaxanthin in "fats and oils" (www.agsci.ubc.ca/courses/fnh/410.colour/330.htm).

Current processes for incorporating carotenoids into water-based beverages or foods involve the use of organic solvents, oils with emulsifiers, high heating, or high-shear mixing. Many of the current processes, particularly in beverages, produce a deposit of the carotenoids around the perimeter of the container in the region of the surface of the treated food or beverage, known as "ringing." Optical clarity is a critical characteristic for many beverage compositions. Various fruit drinks, fruit juices and fortified water drinks have included terms such as "crystal clear" and "fresh" to distinguish their image and marketability. Traditionally, this clarity has been difficult to achieve when carotenoids are added to these aqueous compositions. The use of emulsifiers and oil for the incorporation of carotenoids will commonly result in cloudiness of the final aqueous composition.

Essential oils are volatile oils derived from plant material and usually carry the dominant flavor and aroma of the plant from which they are derived. The essential oils are often principally terpenes, and many contain monoterpenes, a class of terpenes containing two isoprene units and whose molecular structure contains a single saturated or unsaturated carbon ring. The essential oils are a group of oils of interest in the food and personal care industries since most are food grade and most have pleasant flavors and/or aromas. While the flavors or aromas can be strong at times, these oils can be placed into food matrices and it is possible to have the food or beverage mask the aroma. Accordingly, the identification of one or more essential oils that can solubilize a high percentage of one or more carotenoids is important as the desired amount of carotenoid can be delivered with a decreased amount of the essential oil. Of course, by using a decreased amount of the essential oil, it will be easier to mask any undesirable odor or flavor attribute. Surprisingly, essential oils were found to solubilize carotenoids at higher percentages than previously believed possible. The carotenoid/essential oil product can also be used for liposome technology as a delivery system for the carotenoid. This technology will also be good for other delivery systems that require a liquid carrier.

SUMMARY OF THE INVENTION

The present invention comprises surprisingly concentrated solutions of carotenoids in solvents, essential oils and cosmetic oils for use in foods, beverages, and personal care products. The concentrated solutions comprise between about 0.8 weight % and about 8 weight % carotenoid in the oil, or between about 15 times and about 100 times the concentration reported in the prior art. The concentrated solutions are particularly suited for adding carotenoids to foods, beverages, and personal care products. An antioxidant may be added to help in preventing oxidation of the carotenoid. No elevated temperatures, high-shear mixing, or organic solvents are required to form the product.

In a preferred embodiment of the invention, the oils are selected from essential oils and cosmetic oils. Preferred essential oils include bay oil, cornmint oil, peppermint oil, spearmint oil, tea tree oil, and thyme oil. Preferred solvents include thymol and carvacrol, the primary constituents of thyme oil. Preferred cosmetic oils include castor cerester, which, although chemically not an oil, is widely used as an oil substitute in the cosmetic industry and is referred to herein as an oil.

The carotenoids are selected from actinioerythrol, astaxanthin, bixin, canthaxanthin, capsanthin, capsorubin, β-8'-apo-carotenal (apo-carotenal), β-12'-apo-carotenal, α-carotene, β-carotene, "carotene" (a mixture of α- and β-carotenes), γ-carotene, α-cryptoxanthin, β-cryptoxanthin, lutein, lycopene, violerythrin, zeaxanthin, and esters of hydroxyl- or carboxyl-containing members thereof. Preferably, the carotenoids are in crystalline form. Examples of crystalline carotenoids that can be used in the practice of this invention include lutein, β-carotene, α-cryptoxanthin, β-cryptoxanthin, α-carotene, lycopene, astaxanthin, canthaxanthin, and zeaxanthin. The preferred carotenoids include astaxanthin, β-carotene, canthaxanthin, lutein, and zeaxanthin, and most preferably lutein. The oils and the carotenoids may be used singly or in combination; in particular, the carotenoids have solubilities that differ from oil to oil and so combinations of oils may be used to solubilize combinations of carotenoids.

The amount of oil and carotenoid in the composition are selected as amounts that will vary depending upon which form of carotenoid and oil used, their method of preparation, and how much is to be included in the final product. For example a dispersion of lutein in oil will not solubilize as readily in most oils as a corresponding quantity of crystalline lutein.

It may be desired to incorporate an antioxidant into the mixture to assist in the prevention of oxidation of the carotenoid so as to preserve its color and activity. Antioxidants known for use in stabilizing carotenoids include tocopherols, extracts of rosemary, ascorbyl palmitate, citric acid, ascorbic acid, BHA, and BHT.

The carotenoids are added in an amount to create a concentrated product having between about 0.8 weight percent and about 8 weight percent carotenoid(s). When the concentrated product is added to a food or beverage product, the levels of carotenoid present in the final product are between about 0.1 mg and 10 mg per serving, depending on the color desired or the level of supplementation of the carotenoid(s), or both. In a beverage, a preferred range is between about 0.2 mg and 6 mg per 8 oz. In a personal care product, a preferred range is between about 50 ppm to about 5 weight %.

The concentrated product of the present invention is a solution of the carotenoid in the oil. The present invention is particularly suited to the production of fortified beverages, fortified foods, such as ready-to-eat cereals, sports and nutrition bars, bread, and the like, and as colorants or active ingredients in personal care products such as lotions, cleansers, and sun screens.

The products of the present invention are more economical than other compositions that attempt to obtain similar results, specifically in that no organic solvents are required, no heating is required, no high speed or high-shear mixing is required, and a relatively small amount of oils are required. The products are therefore also simpler to formulate and manufacture than those already known for the incorporation of carotenoids into beverages, foods, and personal care products and can be used to give a wider range of products.

It is an object of the present invention to provide a concentrated carotenoid solution that can be added to foods and beverages.

It is another object of the present invention to provide a process for preparing a concentrated carotenoid solution that avoids the use of organic solvents, elevated temperatures, high speed mixing, or high-shear mixing.

It is a further object of the present invention to provide concentrated carotenoid solutions that are physiologically absorbable.

These and other objects of the invention will be made apparent to those skilled in the art upon a review and understanding of this specification, the associated drawings, and the appended claims.

DETAILED DESCRIPTION OF A PREFERRED EMBODIMENT

The process according to the invention is preferably used to prepare concentrated carotenoid solution for use to supplement foods and beverages with carotenoids, for use in coloring personal care products, foods and beverages, and to a process for their preparation.

Examples of carotenoids which can be used according to the invention are the known, available, natural or synthetic representatives of this class of compounds, for example actinioerythrol, astaxanthin, bixin, canthaxanthin, capsanthin, capsorubin, β-8'-apo-carotenal (apo-carotenal), β-12'-apo-carotenal, α-carotene, β-carotene, "carotene" (a mixture of α- and β-carotenes), γ-carotene, α-cryptoxanthin, β-cryptoxanthin, lutein, lycopene, violerythrin, zeaxanthin, and esters of hydroxyl- or carboxyl-containing members thereof. The preferred carotenoids are lutein, zeaxanthin, canthaxanthin, β-carotene, and astaxanthin.

In a preferred embodiment of the invention, the oils are selected from essential oils and cosmetic oils. Preferred essential oils include bay oil, cornmint oil, peppermint oil, spearmint oil, tea tree oil, and thyme oil, as well as thymol and carvacrol, the primary constituents of thyme oil. Preferred cosmetic oils include castor cerester.

An antioxidant can be added to the concentrated product and/or to the carotenoid prior to its addition to the oil. The antioxidant is used to increase the stability of the active ingredient to oxidative breakdown. The antioxidant if used is preferably dissolved together with the carotenoids in the oil. Examples of antioxidants that can be used include tocopherols, extracts of rosemary, ascorbyl palmitate, citric acid, ascorbic acid, BHA, and BHT. Other suitable antioxidants can also be used. The amount of antioxidant to be used depends on the particular antioxidant selected and the environment in which the carotenoid composition is to be used. The range of antioxidant is from about 0.01 to about 0.1 percent by weight, based on the weight of the carotenoid used in the composition.

The concentrated carotenoid products of this invention include from about 0.1 to about 20 percent by weight carotenoid, based on the weight of the concentrated product in liquid form, and between about 1 to about 35 percent by weight carotenoid, based on the weight of the concentrated product in dry form.

Materials and Methods Used in the Experiments

Oils

Oils used for this experiment were obtained from The Lebermuth Company (South Bend, Ind.), Spectrum Botanicals (Blodgett, Oreg.), NOW Foods, (Glendale Heights, Ill.), and Tri-K Industries (Northvale, N.J.). Other solvents and pure monoterpenes were purchased from Fisher and Aldrich. Lutein Dry Cake was obtained from Kemin Foods, L.C., (Des Moines, Iowa). Beta-carotene crystals (purity 99.8%; C9750) were purchased from Sigma. Zeaxanthin crystals (purity 100.1%; Product Code 04 11876 01; Lot# UE00010005) were manufactured by Roche Vitamins. Astaxanthin (purity 98%; Product Code: 011054-0, Lot# 01-011054-811) and canthaxanthin (purity "~10%"; Product Code: 03115-1, Lot# 01-03115–215) were both purchased from Chromadex (Laguna Hills, Calif.). Carvacrol was purchased from Aldrich (Product Code # 282197, Lot # 13403CI) as well as linalool (Prod # L2602, Lot # 02106MI) and p-cymene (Aldrich, Prod # C121452, Lot # 03011BU).

A Hewlett-Packard UV-VIS spectrophotometer (model HP8453) was used to perform the spectroscopy. An Agilent HPLC (model 1100) was used to perform the HPLC analysis.

Tagetes Oil—Lutein Control

The tagetes oil used in the solubility experiments had a definite yellow color. To ensure that the color was not due to lutein being present in the oil, a sample of the untreated tagetes oil was analyzed for lutein content. Tagetes oil in the amount of 0.5231 g was dissolved in 25 ml HEAT (10:6:7:7 v:v:v:v hexane:ethanol:acetone:toluene). Two ml of the HEAT solution was dried under nitrogen and re-dissolved in 2 ml of ethanol. The absorbance of the ethanol solution was read at 446 nm on the UV/VIS spectrophotometer. Although the sample had some absorbance ($A_{446}=0.35072$) at 446 nm, the characteristic triple peak of lutein was not present. There was actually no peak in the region; the recorded absorbance was the tail of a peak with a maximum at 390–400 nm. Even this peak was not completely defined because there was overlapping absorbance from the 200–300 nm region.

The sample was also analyzed by HPLC. There was no peak around 15 minutes in the lutein/zeaxanthin region. There was, however, a small peak at 8.6 minutes with a total area of 1107.2. The conclusion was reached that no free lutein was present in the sample to interfere with the calculation of lutein content solubilized by the oil.

Lutein Solubility in Essential Oils

Lutein dry cake was dissolved in each oil until visibly saturated. The sample was then blanketed with argon and sonicated for ten minutes. If the all the lutein appeared to go into solution, more was added and the process repeated. After the sample was completely saturated, the sample was transferred to a microcentrifuge tube and centrifuged at 14,000 rpm for 10 minutes. If the lutein was not pelleted by centrifugation, the sample was passed through a 0.22 μm filter unit to remove any suspended lutein. The clarified oil was then analyzed for lutein content using UV-VIS and HPLC.

Lutein content was measured by using an analytical method as follows. Using an analytical balance, 10–20 mg of the sample is weighed into a 100 ml volumetric flask. The sample is diluted to the mark with HEAT (10:6:7:7 v:v:v:v hexane:ethanol:acetone:toluene), and the mixture is agitated or stirred until the sample is dissolved. One ml of this solution is transferred by pipette into a 100 ml amber volumetric flask and diluted to the mark with ethanol. The absorbance of the ethanol solution is measured at 446 nm on a UV/Vis spectrophotometer that has previously been zeroed against ethanol. For analysis by HPLC, 1 ml of the ethanol solution is transferred to an HPLC sample vial and dried using a nitrogen or argon gas stream. The dried sample is dissolved in 1 ml of HPLC mobile phase; sonication may be necessary to complete the solution. The HPLC instrument is set with the following parameters: the column is a 25 cm×4.6 mm nitrile bonded Spherisorb with 5 μm particles; 69 minute run time; flow rate of 1.00 ml/min; back pressure of 64 bar; injection volume of 50 μl; solvent of 75:25:0.35:0.1 (v:v:v:v) hexane/methylene chloride/methanol/diisopropylethylamine (all solvents are HPLC grade); detector is a visible lamp set to 446 nm; and temperature is 22° C. Fifty μl of the ethanol solution is injected into the HPLC column. The peaks at approximately 24, 26, 28.5, 32, 34, 40 and 42 minutes (corresponding to 13, 13'-di-cis-lutein, all-trans-lutein, all-trans-zeaxanthin, 9-cis-lutein, 9'-cis-lutein, 13 and 13'-cis -lutein and 9-cis-zeaxanthin) are integrated and used to determine the HPLC percent area for the lutein peak. The following equations were used for the essential oils:

*UV-VIS* for Lutein

% Carotenoids (w/w) =

$$\frac{A_{446} * \text{HEAT vol (ml)} * \text{EtOH dilution factor}}{A^{1\%} * \text{sample mass (g)} * 100} * 100\%$$

$A^{1\%} = 2550$

HPLC for Lutein

% Lutein=% Carotenoids*(% Total HPLC area of lutein/100)

Beta-Carotene Solubility in Essential Oils

Beta-carotene was dissolved in each oil until visibly saturated. The sample was then blanketed with argon and sonicated for ten minutes. When the sample was completely saturated, the solution was transferred to a micro centrifuge tube and centrifuged at 14,000 rpm for 10 minutes. The clarified oil was then analyzed for beta-carotene content. The method for analyzing lutein crystals, with a few modifications, was used to analyze beta-carotene. First, methylene chloride was substituted for HEAT when dissolving the samples. Second, when determining total carotenoids, the absorbance was measured at 453 nm rather than 446 nm.

*UV/VIS* for Beta-Carotene

% Carotenoids (w/w) =

$$\frac{A_{453} * \text{MethCl vol (ml)} * \text{EtOH dilution factor}}{A^{1\%} * \text{sample mass (g)} * 100} * 100\%$$

$A^{1\%} = 2620$

HPLC for Beta Carotene

% Beta Carotene=% Carotenoids*(% Total HPLC area of Beta Carotene/100)

Zeaxanthin Solubility in Essential Oils

Zeaxanthin was dissolved in each oil until visibly saturated. The sample was then blanketed with argon and sonicated for ten minutes. When the sample was completely saturated, the solution was transferred to a micro centrifuge tube and centrifuged at 14,000 rpm for 10 minutes. The clarified oil was then analyzed for zeaxanthin content. The method for analyzing lutein crystals was used to analyze zeaxanthin, however, a few modifications were made. First, methylene chloride was substituted for HEAT when dissolving the samples. It was noted in an earlier trial that zeaxanthin was not as soluble as lutein in HEAT. When determining total carotenoids, the absorbance was measured at 450 nm rather than 446 nm.

*UV/VIS* for Zeaxanthin

% Carotenoids (w/w) =

$$\frac{A_{450} * \text{HEAT vol (ml)} * \text{EtOH dilution factor}}{A^{1\%} * \text{sample mass (g)} * 100} * 100\%$$

$A^{1\%} = 2540$

HPLC for Zeaxanthin

% Zeaxanthin=% Carotenoids*(% Total HPLC area of zeaxanthin/100)

Astaxanthin in Essential Oils

Astaxanthin was dissolved in each oil until visibly saturated. The sample was then blanketed with argon and sonicated for ten minutes. When the sample was completely saturated, the solution was transferred to a micro centrifuge tube and centrifuged at 14,000 rpm for 10 minutes. The clarified oil was then analyzed for astaxanthin content. The method for analyzing lutein crystals was used to analyze astaxanthin, however, a few modifications were made. First, methylene chloride was substituted for HEAT when dissolving the samples. It was noted in an earlier trial that astaxanthin was not as soluble as lutein in HEAT. When determining total carotenoids, the absorbance was measured at 470 nm rather than 446 nm.

HPLC for Astaxanthin $$\% \text{ Astaxanthin } (w/w) = \frac{A_{470} * Vol_{Hexane} \text{ (ml)}}{\text{sample mass (g)} * A_{1\,cm}^{1\%}}$$

$A_{1\,cm}^{1\%} = 2100 \; (\lambda = 470 \text{ nm})$

Canthaxanthin in Essentials Oils

Canthaxanthin was dissolved in each oil until visibly saturated. The sample was then blanketed with argon and sonicated for ten minutes. When the sample was completely saturated, the solution was transferred to a microcentrifuge tube and centrifuged at 14,000 rpm for 10 minutes. The clarified oil was then analyzed for canthaxanthin content. The method for analyzing lutein crystals was used to analyze canthaxanthin, however, a few modifications were made. First, methylene chloride was substituted for HEAT when dissolving the samples. It was noted in an earlier trial that canthaxanthin was not as soluble as lutein in HEAT. When determining total carotenoids, the absorbance was measured at 466 nm rather than 446 nm.

$$\% \text{ Canthaxanthin } (w/w) = \frac{A_{466} * Vol_{Hexane} \text{ (ml)}}{\text{sample mass (g)} * A_{1\,cm}^{1\%}}$$

$A_{1\,cm}^{1\%} = 2200 \; (\lambda = 466 \text{ nm})$

Results and Discussion

Twenty-eight oils from Lebermuth were tested for lutein solubility and the results are shown in Table 1. Red thyme, white thyme, and pure thyme oil had the best overall lutein solubility ranging from 3.0–4.7%, with red thyme having the highest. Other oils having greater than 1.0% lutein solubility included peppermint, spearmint, cornmint, tea tree, and bay oil. Wintergreen oil, interestingly, had a very low lutein solubility of 0.226%, even though all the other mint oils had solubilities above 1%. The citrus oils (white grapefruit, lemon, and lime all had very low solubilities ranging from 0.071–0.21%. Other oils such as cedarwood, nutmeg, and aloe vera also had low solubilities. Latin species names of plants and the oil grades are found in Appendix A.

TABLE 1

Lutein solubility in essential oils.

| Sample | Item # | Lot # | % Carotenoids | % Lutein |
|---|---|---|---|---|
| Aloe Vera LQX | 50-6010-11 | Sample | 0.032 | 0.028 |
| Anise, Spanish | 50-6015-11 | Sample | 0.248 | 0.223 |
| Bay | 50-6025-01 | Sample | 1.263 | 1.152 |
| Bay | 50-6025-01 | BA41-0484 | 1.143 | 1.001 |
| Bergamot Mint | 50-6177-01 | Sample | 0.361 | 0.325 |
| Birch, Sweet Southern | 50-6035-02 | Sample | 0.262 | 0.236 |
| Cassia, redistilled | 50-6060-01 | Sample | 0.674 | 0.639 |
| Cedarwood, Texas White | 50-6075-01 | Sample | 0.191 | 0.172 |
| Cornmint, Redistilled | 50-6100-01 | Sample | 1.282 | 1.163 |
| Cornmint, Redistilled | 50-6100-01 | CR43-0155 | 1.065 | 0.951 |
| Eucalyptus, 80/85 | 50-6105-02 | Sample | 0.754 | 0.672 |
| Eugenol | 50-6110-01 | Sample | 0.567 | 0.517 |
| Frankincense, Olibanum | 50-5100-01 | Sample | 0.264 | 0.243 |
| Geranium (Rose), Egyptian | 50-6130-11 | Sample | 0.665 | 0.600 |

TABLE 1-continued

Lutein solubility in essential oils.

| Sample | Item # | Lot # | % Carotenoids | % Lutein |
|---|---|---|---|---|
| Grapefruit, White | 50-6140-01 | Sample | 0.078 | 0.071 |
| Juniperberry | 50-6150-02 | Sample | 0.155 | 0.140 |
| Lemon, California | 50-6160-01 | Sample | 0.079 | 0.071 |
| Lime, distilled | 50-6170-01 | Sample | 0.234 | 0.213 |
| Nutmeg | 50-6190-01 | Sample | 0.134 | 0.122 |
| Peppermint, Yakima redistilled | 50-6225-21 | Sample | 1.136 | 1.010 |
| Peppermint, Yakima redistilled | 50-6225-21 | PY43-0157 | 1.062 | 0.945 |
| Rosemary, Morrocan | 50-6230-03 | Sample | 0.713 | 0.637 |
| Sage, Clary | 50-6235-03 | Sample | 0.324 | 0.294 |
| Spearmint, redistilled | 50-6250-11 | Sample | 1.124 | 1.001 |
| Spearmint, redistilled | 50-6250-11 | 39SR-0163 | 1.253 | 1.124 |
| Tagetes | 50-6261-01 | Sample | 0.296 | 0.268 |
| Tea Tree | 50-6270-01 | TX43-0146 | 0.981 | 0.877 |
| Thyme, Pure | 50-6275-04 | TP41-0053 | 3.876 | 3.453 |
| Thyme, Red | 50-6275-02 | TR43-0158 | 5.349 | 4.753 |
| Thyme, White | 50-6275-01 | TLC11-T477 | 3.707 | 3.095 |
| Wintergreen, Natural | 50-6285-11 | Sample | 0.245 | 0.226 |
| Wormwood, Natural | 50-6290-01 | Sample | 0.754 | 0.682 |

Table 2 list the solubility of lutein in oils tested from NOW Foods (Bloomingdale, Ill.), obtained from a health food store. The thyme oil, which was not specified as either red or white but appeared to be white thyme oil, solubilized lutein at 2.5% and tea tree at about 1%. This corresponded well with the Lebermuth supplier. Other oils such as grapeseed, almond, and apricot kernel had very low solubilities at about 0.02–0.03%. These oils, however, did not seem to have as strong an odor and so may be fixed oils or "cut" and not "true" essential oils.

TABLE 2

Lutein solubility in NOW Foods brand oils.

| Sample | Item # | Lot # | % Carotenoids | % Lutein |
|---|---|---|---|---|
| Almond | 7660 | unlabeled | 0.034 | 0.030 |
| Apricot Kernel | 7665 | unlabeled | 0.039 | 0.035 |
| Castor | 7675 | unlabeled | 0.187 | 0.171 |
| Grapeseed | 7705 | unlabeled | 0.030 | 0.027 |
| Tea Tree | 7625 | unlabeled | 1.182 | 1.084 |
| Thyme | 7635 | unlabeled | 3.917 | 3.582 |

Table 3 shows the results obtained from Spectrum Botanical Company. The peppermint and spearmint oils had slightly higher solubilities than the Lebermuth supplier. This could be due to variations in the processing. White thyme oil from Spectrum was 4.9% while white thyme oil from Lebermuth was 3.0%. Both species were labeled as *Thymus vulgaris*. Spectrum has two oils they call "red thyme oil", *Thymus vulgaris* and *Thymus satureioides*. The *Thymus satureioides* was much lower than the *Thymus vulgaris* red thyme oil (1.0 vs 4.4%). Care should be exercised to verify the species when specifying thyme oils.

TABLE 3

Lutein solubility in Spectrum Botanical Company essential oils.

| Sample | Item # | Lot # | % Carotenoids | % Lutein |
|---|---|---|---|---|
| Bay | EO6 | unlabeled | 1.477 | 1.327 |
| Peppermint | EO64 | unlabeled | 1.521 | 1.358 |
| Spearmint | EO76 | unlabeled | 1.478 | 1.325 |
| Tea Tree | EO80 | unlabeled | 1.053 | 0.942 |
| Red Thyme *Thymus vulgaris* | EO151 | unlabeled | 4.989 | 4.481 |
| Red Thyme *Thymus satureioides* | unspecified | unlabeled | 1.207 | 1.084 |
| White Thyme | EO82 | unlabeled | 5.483 | 4.903 |
| White Thyme (from private source) | unspecified | unlabeled | 5.840 | 5.068 |

Table 4 displays the gas chromatograph profile results obtained from samples analyzed by a private lab. D-limonene and carvacrol was found to be higher in the Spectrum Oils (both red and white). D-limonene, 1,8-cineole, and carvacrol are all liquids at room temperature. Thymol is actually a solid at room temperature. Gas chromatograph profiles were also obtained form The Lebermuth Company on their three thyme oils. Results of Lebermuth's gas chromatograph analysis can be found in Appendix B. All the constituents that were liquids at room temperature and that were available commercially were listed.

In order to determine if a single constituent was responsible for solubilizing lutein, carvacrol, linalool, p-cymene, and limonene were purchased from Aldrich and the same solubility experiments were performed. Results of the pure compound analysis are shown in Table 5. Beta-carotene and zeaxanthin were also tested. Of all four pure compounds tested, carvacrol not only had the highest lutein solubility (7.8%), but also solubilized more lutein then any of the thyme oils did as mixtures. The response, however, is not linear with carvacrol content, so there may be some kind of combination effect with the other liquids and/or solids present in the oils. P-cymene actually solubilized more beta-carotene then lutein or zeaxanthin.

TABLE 4

Gas chromatography results on thyme essential oil content.

| Product | Solubility (w/w) | | GC Results (w/w %) | | | |
|---|---|---|---|---|---|---|
| | % TC* | % Lutein | limonene | 1,8-Cineole (eucalyptol) | thymol | carvacrol |
| Lebermuth Red Thyme oil | 5.349 | 4.753 | 0.4471 | 32.5106 | 48.9951 | 0.3120 |
| Spectrum Red Thyme oil | 4.989 | 4.481 | 5.0354 | 22.1014 | 45.0620 | 2.3182 |
| Lebermuth White Thyme oil | 3.707 | 3.095 | 0.5423 | 21.2630 | 48.5249 | 0.0126 |
| Spectrum White Thyme oil | 5.483 | 4.903 | 4.4526 | 25.9153 | 46.3850 | 5.5036 |
| Lebermuth Pure Thyme oil | 3.876 | 3.453 | not tested | not tested | not tested | not tested |

*Total Carotenoids

HPLC values as weight percentages were calculated using the extinction coefficients from the literature. The chromatograms were also checked to see that no other carotenoid contaminants were found in the ordered products. The carvacrol values for lutein, zeaxanthin, and beta-carotene are found in Table 5.

TABLE 5

Solubility in pure compounds isolated from thyme oil and available commercially.

| Monoterpene (C10) | % lutein | % beta-carotene | % zeaxanthin |
|---|---|---|---|
| Pure carvacrol | 7.82 | 0.10 | 2.99 |
| Pure linalool | 0.359 | 0.030 | 0.21 |
| Pure p-cymene | 0.031 | 0.20 | 0.012 |
| d-limonene | 0.027 | not tested | not tested |

Beta-carotene, a hydrocarbon carotenoid, was also evaluated in the oils that lutein was soluble in the most (red thyme, white thyme, pure thyme, cornmint, spearmint, peppermint, tea tree, and bay oil). Results are shown in Table 6. Spearmint oil was the best of the group (~0.5%), but did not come close to the lutein value (~1.0%). Bay oil performed the worst (0.16%). Lutein in bay oil came out at 1%. Xanthophylls, which are frequently referred to as oxygenated carotenoids, may be more soluble in these types of oils than other hydrocarbon carotenoids.

TABLE 6

Beta-carotene solubility in selected essential oils.

| Sample | Item # | Lot # | % Carotenoids | % Beta-Carotene |
|---|---|---|---|---|
| Bay | 50-6025-01 | BA41-0484 | 0.163 | 0.163 |
| Cornmint, redistilled | 50-6100-01 | CR43-0155 | 0.252 | 0.252 |
| Peppermint, Yakima redistilled | 50-6225-21 | PY43-0157 | 0.263 | 0.263 |
| Spearmint, redistilled | 50-6250-11 | 39SR-0163 | 0.532 | 0.532 |
| Tea Tree | 50-6270-01 | TX43-0146 | 0.427 | 0.427 |
| Thyme, Pure | 50-6275-04 | TP41-0053 | 0.245 | 0.245 |
| Thyme, Red | 50-6275-02 | TR43-0158 | 0.267 | 0.267 |
| Thyme, White | 50-6275-01 | TLC11-T477 | 0.273 | 0.273 |

Zeaxanthin, a xanthophyll, ran contrary to the aforementioned theory of solubility. Zeaxanthin, with just a double bond shift (and two hydroxyls like lutein) was less than 1% soluble in all of the oils except the thyme oils. Even the thyme oil solubility of zeaxanthin (~1%) was much lower than lutein (3.5–5%) (Table 7).

TABLE 7

Zeaxanthin solubility in selected essential oils.

| Sample | Item # | Lot # | % Carotenoids | % Zeaxanthin |
|---|---|---|---|---|
| Bay | 50-6025-01 | BA41-0484 | 0.281 | 0.276 |
| Cornmint, redistilled | 50-6100-01 | CR43-0155 | 0.403 | 0.397 |
| Peppermint, Yakima redistilled | 50-6225-21 | PY43-0157 | 0.452 | 0.446 |
| Spearmint, redistilled | 50-6250-11 | 39SR-0163 | 0.374 | 0.369 |
| Tea Tree | 50-6270-01 | TX43-0146 | 0.364 | 0.361 |
| Thyme, Pure | 50-6275-04 | TP41-0053 | 0.920 | 0.916 |
| Thyme, Red | 50-6275-02 | TR43-0158 | 1.063 | 1.059 |
| Thyme, White | 50-6275-01 | TLC11-T477 | 1.049 | 1.043 |
| Tea Tree (NOW) | 7625 | unlabeled | 0.398 | 0.394 |
| Thyme, White (NOW) | 7635 | unlabeled | 0.784 | 0.782 |

Astaxanthin and canthaxanthin, both xanthophylls found in human serum, were also tested in a few select oils (spearmint, white thyme and carvacrol) to determine if any structure activity relationships could be made with lutein and the other carotenoids. Astaxanthin is basically zeaxanthin with two carbonyls at the 4 and 4' positions. Canthaxanthin is basically astaxanthin absent the two hydroxyl groups. Results of astaxanthin are shown in Table 8 and canthaxanthin results are shown in Table 9. Astaxanthin and canthaxanthin had very low solubility when compared to lutein. Astaxanthin was 33 times less soluble in spearmint oil than lutein and 16 times less soluble than lutein in white thyme oil. Carvacrol did not solubilize astaxanthin to a great extent (~0.24%). Canthaxanthin was even less soluble than lutein for these three oils. Canthaxanthin was about 350 times less soluble in spearmint oil and 3900 times less soluble than lutein in carvacrol. Chemical structures of all compounds are found in Appendix C.

TABLE 8

Astaxanthin solubility in selected essential oils.

| Sample | Item # | Lot # | % Astaxanthin by HPLC |
|---|---|---|---|
| Spearmint oil | 05-6250-11 | SP43-0208 | 0.0301 |
| Thyme oil, White | 05-6275-01 | TLC11-T049 | 0.1876 |
| Carvacrol (clear oil) | 282-197 | 13403CI | 0.2420 |

TABLE 9

Canthaxanthin solubility in selected essential oils.

| Sample | Item # | Lot # | % Canthaxanthin by HPLC |
|---|---|---|---|
| Spearmint oil | 05-6250-11 | SP43-0208 | 0.0028 |
| Thyme oil, White | 05-6275-01 | TLC11-T049 | 0.0036 |
| Carvacrol (clear oil) | 282-197 | 13403CI | 0.0020 |

Experiments were performed on some commercial cosmetic oils, and the results are shown in Table 10. A slightly different methodology was used in this experiment. UV-VIS was used by itself, not in conjunction with HPLC, so only percentage carotenoids is shown. Measuring the peak area by HPLC would have been useful to determine the actual lutein solubility and not "dry cake" solubility. It is probably safe to assume however, that most of the absorbance at 446 nm will be lutein or zeaxanthin. Of all the cosmetic oils tested, castor ceresters solubilized the most carotenoids (~0.2–0.39%) but did not surpass the essential oils.

TABLE 10

Dry cake solubility in cosmetic oils (FloraGLO lutein dry cake).

| Cosmetic Oil | Supplier | % Carotenoids* (unfiltered) | % Carotenoids* (filtered) | % Carotenoids* (centrifuged) |
|---|---|---|---|---|
| Sophium MC-30 | Tri-K Ind. | not a good solvent | | |
| Biophytosebum | Tri-K Ind. | 0.7605 | 0.0295 | 0.0436 |
| Phytosgualan | Tri-K Ind. | not a good solvent | | |
| Castor Ceresters | Tri-K Ind. | 0.6081 | 0.2454 | 0.3887 |
| Glossamer | Tri-K Ind. | not a good solvent | | |
| Jojoba Oil | Tri-K Ind. | 0.7663 | 0.0240 | 0.0140 |
| Olive Ceresters | Tri-K Ind. | 0.5395 | 0.0637 | 0.0647 |

* % Carotenoids is by weight (UV-VIS data only)

A comparison of essential oils to common solvents was warranted so lutein, zeaxanthin, and beta-carotene were assayed using the same methodology as the essential oils. Results of the common solvents are shown in Table 11.

TABLE 11

Lutein, beta-carotene, and zeaxanthin, solubility in common laboratory solvents.

| Common Solvent | Lutein % w/w | Lutein mg/ml | Beta carotene % w/w | Beta carotene mg/ml | Zeaxanthin % w/w | Zeaxanthin mg/ml |
|---|---|---|---|---|---|---|
| Acetone | 0.377 | 2.96 | — | 0.137 | — | 1.560 |
| Diethyl ether | — | 1.923 | — | 0.712 | — | 1.241 |
| Ethanol | 0.171 | 1.312 | 0.005 | 0.039 | 0.112 | 0.871 |
| Ethyl Acetate | 0.329 | 2.872 | 0.056 | 0.495 | 0.202 | 1.818 |
| HEAT solvent | 2.339 | 17.010 | — | 0.851 | 0.457 | 3.409 |
| Hexane | 0.001 | 0.0095 | 0.115 | 0.761 | 0 | 0.003 |
| Isopropanol | 0.123 | 0.933 | 0.006 | 0.046 | 0.129 | 0.999 |
| Methylene Chloride | — | 16.51 | — | 9.538 | — | 7.301 |
| Propylene Glycol | 0.002 | 0.022 | 0.001 | 0.006 | — | — |
| Tetrahydrofuran (THF) | 12.38 | 110.1 | — | 14.469 | — | 33.29 |

Table 11 displays the data obtained from testing lutein, beta-carotene, and zeaxanthin solubility in common solvents.

The volatile solvents like diethyl ether, dichloromethane, and THF were hard to measure weight percentage basis, so mg/ml was used instead. Zeaxanthin in propylene glycol had a large amount of interference in the UV-VIS scan. The typical carotenoid triplet was not present and a large noisy spectrum interfered with the 450 nm reading, and so it was not reported. THF and dichloromethane were the best two solvents for lutein, beta-carotene, and zeaxanthin. Hexane was a fairly good solvent for beta-carotene, but a very poor solvent for lutein and zeaxanthin. This is not surprising because beta-carotene is a hydrocarbon and not a xanthophyll.

Stability experiments were performed with the best group of essential oils and lutein dry cake. Fresh samples were made, placed in amber vials, blanked with argon and placed onto stability at 25° C. and 40° C. after taking initial % carotenoids and % lutein. Bay, cornmint, peppermint, spearmint, tea tree, pure thyme, red thyme, and white thyme oils were all tested up to 20 weeks. FIGS. 1 and 2 show total carotenoids at ambient and FIGS. 3 and 4 show all trans lutein at ambient conditions. Tea tree oil and bay oil had the best stability of total carotenoids and all trans lutein at ambient conditions. Tea tree lost 32% lutein and pure thyme lost 22% lutein after 20 weeks. It should be noted that the oils were not tested at maximum lutein solubility conditions for stability testing.

FIGS. 5 and 6 show the same set of experiments for total carotenoids at accelerated conditions. FIGS. 7 and 8 show all trans lutein at accelerated conditions. Under accelerated conditions, bay oil, red thyme and pure thyme fared the best for total carotenoids and lutein. Bay oil trans lutein dropped 54% and pure/red thyme oil trans lutein dropped approximately 47% at 20 weeks. It seems the biggest drop occurs during the first 2-week time point then it levels off. All other oils did much worse. Total carotenoids were fairly steady at accelerated conditions, which shows that cis isomerization is occurring.

Conclusion

This disclosure shows solubility data for lutein, beta-carotene, and zeaxanthin in essential oils as well as some limited data with astaxanthin and canthaxanthin. Essential oils, common solvents, and some cosmetic oil data were all obtained with lutein. The best overall essential oils for lutein are the thyme oils (red, white, and pure) and have the highest lutein solubility (3–5%). If the thyme oil is broken down into pure constituents, carvacrol has the highest lutein solubility at about 7.8%. Spearmint, peppermint, cornmint, tea tree and bay oil all had lutein solubilities about 1%. Zeaxanthin, lutein's sister compound, did not go into solution as well as lutein for the mint oils, the thyme oils, and many others. Astaxanthin and canthaxanthin, two other xanthophylls, did not have comparable solubilities when compared to lutein in spearmint oil, white thyme oil, and carvacrol. Adding the two ketone groups to the lutein molecule (astaxanthin and canthaxanthin) appears to inhibit solubility.

Stability was observed for lutein in eight oils at ambient and accelerated temperature. Cis lutein isomerization did occur more rapidly in the tea tree and bay oils. Overall stability at ambient showed that tea tree lost 32% lutein and pure thyme lost 22% lutein over 20 weeks. At 40° C., the mints (spearmint, peppermint, and cornmint lost total carotenoids at a much faster rate than tea tree, bay and the thyme oils. The first 2 weeks tended to show the largest drop off for both total carotenoids and trans lutein.

APPENDIX A

| Lebermuth Co. Oils: | Plant Latin Name | Centrifuged or Filtered | Oil Grade* |
|---|---|---|---|
| Aloe Vera LQX | Aloe vera | Centrifuged | PG |
| Anise, Spanish | Pimpinella anisum | Centrifuged | CG |
| Bay | Pimenta citrata | Centrifuged | PG/K |
| Bergamot Mint | Mentha citrata | Centrifuged | PG |
| Birch, Sweet Southern | — | Filtered | CG |
| Cassia, redistilled | Cinnamomum cassia | Filtered | CG |
| Cedarwood, Texas White | Juniperus ashei | Centrifuged | CG |
| Cornmint, Redistilled | Mentha arvensis | Centrifuged | PG/K |
| Eucalyptus, 80/85 | Eucalyptus globules | Centrifuged | PG |
| Eugenol | pure compound | Filtered | PG |
| Frankincense, Olibanum | Bosellia serrata | Centrifuged | PG |
| Geranium (Rose), Egyptian | — | Filtered | CG |
| Grapefruit, White | Citrus paradisa | Centrifuged | PG |
| Juniperberry | Juniperus communis | Centrifuged | PG |
| Lemon, California | Citrus limon | Centrifuged | PG/K |
| Lime, distilled | Citrus aurantifolia | Centrifuged | PG |
| Nutmeg | Myristica fragrens | Centrifuged | PG |
| Peppermint, Yakima redistilled | Mentha piperita | Centrifuged | CG/K |
| Rosemary, Morrocan | Rosmarinus officinalis | Centrifuged | PG |
| Sage, Clary | Salvia sclarea | Centrifuged | PG |
| Spearmint, redistilled | Mentha spicata | Centrifuged | CG/K |
| Tagetes | Tagetes minuta | Centrifuged | PG |
| Tea Tree | Melaleuca alternifolia | Centrifuged | PG |
| Thyme, Pure | Thymus vulgaris | Centrifuged | PG |
| Thyme, Red | Thymus vulgaris | Centrifuged | CG |
| Thyme, White | Thymus vulgaris | Centrifuged | CG |
| Wintergreen, Natural | Gaultheria procumbens | Filtered | PG |
| Wormwood, Natural | Artemisia absinthium | Centrifuged | PG |
| Bay | Pimenta racemosa | Centrifuged | unspecified |
| Peppermint | Mentha piperita | Centrifuged | unspecified |
| Spearmint | Mentha spicata | Centrifuged | unspecified |
| Tea Tree | Melaleuca alternifolia | Centrifuged | unspecified |
| Red Thyme | Thymus vugaris | Centrifuged | unspecified |
| Red Thyme | Thymus satureioides | Centrifuged | unspecified |
| White Thyme | Thymus vulgaris | Centrifuged | unspecified |

*PG = pure grade;
CG = commercial grade;
K = Kosher

APPENDIX B

| Compound | Lebermuth, Co. Percentage by GC | | |
|---|---|---|---|
| | White thyme oil | Pure thyme oil | Red thyme oil |
| 1-octen-3-ol | | 0.57 | |
| 2-isopropyl-1-methoxy-4methylbenzene | | 0.43 | 0.11 |
| 3-carene | 1.45 | | |
| alpha copaene | 0.16 | | |
| alpha fenchene | | 0.14 | 0.27 |
| alpha humulene | | 0.69 | 0.15 |
| alpha pinene | 4.58 | 3.24 | 2.77 |
| alpha terpinene | 0.54 | 0.77 | 0.25 |
| alpha terpineol | 2.08 | 0.16 | 0.62 |
| alpha thujene | | | |
| beta caryophyllene | 3.59 | 5.61 | 1.34 |
| beta myrcene | 1.03 | 2.09 | 1.19 |
| beta pinene | 1.75 | 0.26 | 0.17 |
| borneol | 2.17 | 0.75 | 1.1 |
| bornyl acetate | | 0.07 | |
| camphene | | 1.58 | 0.92 solid |
| camphor | | 0.20 | 0.38 solid |

APPENDIX B-continued

| Compound | Lebermuth, Co. Percentage by GC | | | |
|---|---|---|---|---|
| | White thyme oil | Pure thyme oil | Red thyme oil | |
| carvacrol | | 1.71 | 1.25 | liquid |
| carvone | 0.13 | | | |
| caryphyllene oxide | | 0.71 | | |
| cis-ocimene | 0.12 | | | |
| eucalyptol (1,8 cineole) | 3.43 | 1.14 | 0.67 | liquid |
| gamma terpinene | 0.77 | 4.27 | 0.35 | |
| isobornyl acetate | 0.89 | | 0.45 | |
| limonene | 2.56 | 0.60 | 1.10 | liquid |
| linalool | 4.79 | 7.00 | 6.65 | liquid |
| linalyl acetate | 1.81 | 0.20 | | |
| menthofuran | 0.26 | | | |
| menthol | 0.37 | | | |
| 1-menthone | 0.83 | | | |
| p-cymene | 24.82 | 16.66 | 36.94 | liquid |
| sabinene | 0.81 | | | |
| terpinolene | 0.37 | | | |
| thymol | 39.53 | 47.72 | 42.43 | solid |
| Total | 98.84 | 96.57 | 99.11 | |
| # components | 24 | 23 | 20 | |

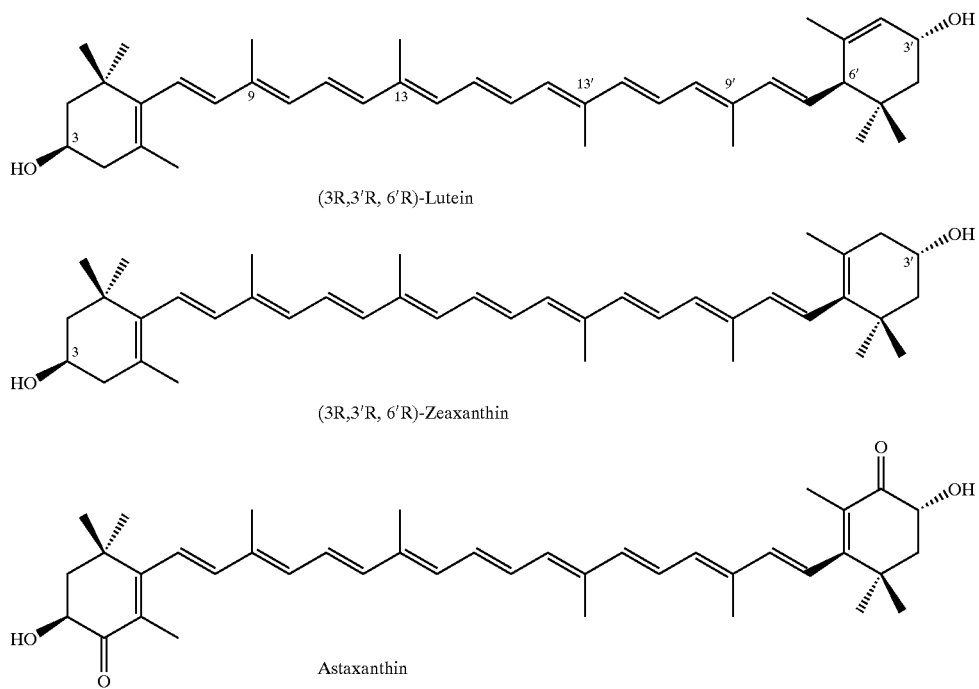

Appendix C (3R,3'R, 6'R)-Lutein (3R,3'R, 6'R)-Zeaxanthin

Astaxanthin

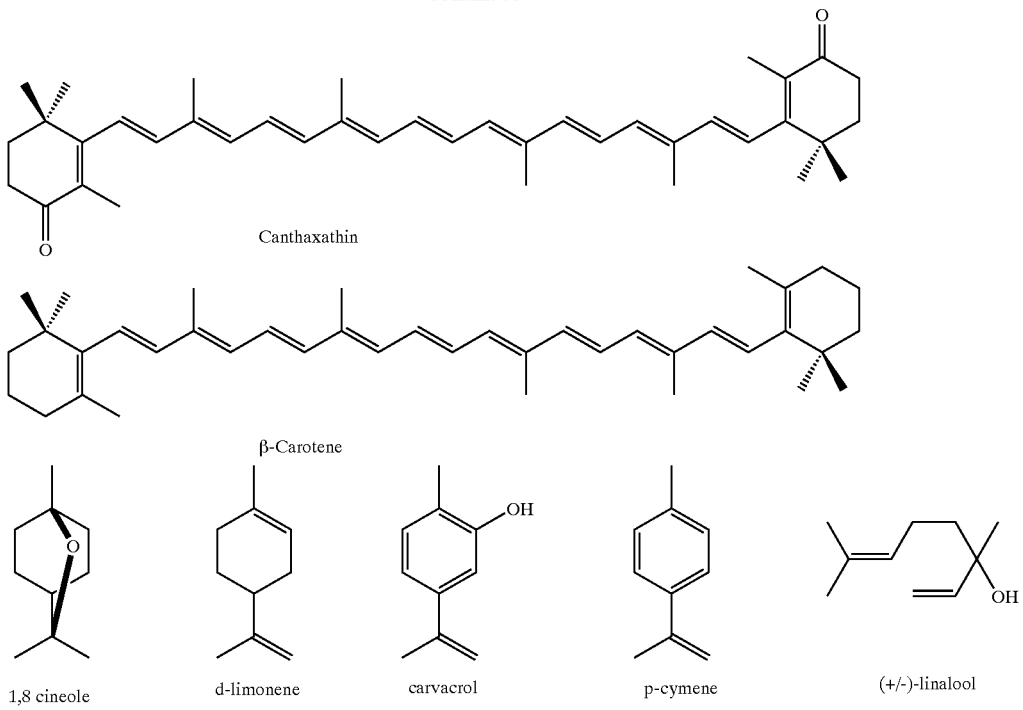

We claim:

1. A food or beverage product supplemented with between about 0.00004% and about 0.0042% of a solubilized carotenoid wherein the solubilized carotenoid is derived from the addition of between about 1.0 mg and about 1.5 g of an emulsifier-free, carotenoid-containing oil per 8 oz. serving.

2. A food or beverage product as defined in claim 1, wherein the carotenoid is selected from the group consisting of actinioerythrol, astaxanthin, bixin, canthaxanthin, capsanthin, capsorubin, β-8'-apo-carotenal (apo-carotenal), β-12'-apo-carotenal, α-carotene, β-carotene, "carotene" (a mixture of α- and β-carotenes), γ-carotene, α-cryptoxanthin, β-cryptoxanthin, lutein, lycopene, violerythrin, zeaxanthin, and esters of hydroxyl- or carboxyl-containing members thereof.

3. A food or beverage product as defined in claim 1, wherein the oil is selected from the group consisting of bay oil, cornmint oil, peppermint oil, spearmint oil, tea tree oil, thyme oil, and castor cerester.

4. A food or beverage product supplemented with between about 0.00004% and about 0.0042% of a solubilized carotenoid wherein the solubilized carotenoid is derived from the addition of between about 1.0% and about 20% of a solution of a carotenoid and a solvent selected from the group consisting of thymol and carvacrol.

* * * * *